US009937138B2

(12) United States Patent
Rii et al.

(10) Patent No.: US 9,937,138 B2
(45) Date of Patent: Apr. 10, 2018

(54) ENHANCER OF SURVIVAL OF TRANSPLANTED ORGAN

(71) Applicants: SBI Pharmaceuticals Co., Ltd., Minato-ku, Tokyo (JP); National Center for Child Health and Development, Setagaya-ku, Tokyo (JP)

(72) Inventors: Ko Rii, Tokyo (JP); Kiwamu Takahashi, Tokyo (JP); Naomi Haga, Tokyo (JP); Fuminori Abe, Tokyo (JP); Tohru Tanaka, Tokyo (JP); Motowo Nakajima, Minato-ku (JP); Hidenori Ito, Minato-ku (JP)

(73) Assignees: National Center for Child Health and Development, Tokyo (JP); SBI Pharmaceuticals Co., Ltd., Tokyo (JP)

( * ) Notice: Subject to any disclaimer, the term of this patent is extended or adjusted under 35 U.S.C. 154(b) by 17 days.

(21) Appl. No.: 15/064,884

(22) Filed: Mar. 9, 2016

(65) Prior Publication Data

US 2016/0206582 A1  Jul. 21, 2016

Related U.S. Application Data

(62) Division of application No. 14/350,488, filed as application No. PCT/JP2012/005782 on Sep. 12, 2012, now Pat. No. 9,314,443.

(30) Foreign Application Priority Data

Oct. 12, 2011 (JP) .................................. 2011-225384
Jul. 13, 2012 (JP) .................................. 2012-157374

(51) Int. Cl.
| | | |
|---|---|---|
| *A61K 31/195* | (2006.01) | |
| *A61K 31/197* | (2006.01) | |
| *A61K 33/26* | (2006.01) | |
| *A61K 31/22* | (2006.01) | |
| *A61K 31/295* | (2006.01) | |
| *A61K 45/06* | (2006.01) | |
| *A01N 1/02* | (2006.01) | |
| *A61K 35/17* | (2015.01) | |
| *A61K 35/12* | (2015.01) | |

(52) U.S. Cl.
CPC .......... *A61K 31/197* (2013.01); *A01N 1/0226* (2013.01); *A61K 31/22* (2013.01); *A61K 31/295* (2013.01); *A61K 33/26* (2013.01); *A61K 35/17* (2013.01); *A61K 45/06* (2013.01); *A61K 2035/122* (2013.01); *A61K 2035/124* (2013.01)

(58) Field of Classification Search
CPC .... A61K 31/197; A61K 31/22; A61K 31/295; A61K 33/26; A61K 2035/122; A61K 2035/124; A61K 35/17; A61K 45/06; A01N 1/0226

USPC .................................................. 514/561, 502
See application file for complete search history.

(56) References Cited

U.S. PATENT DOCUMENTS

| | | | |
|---|---|---|---|
| 5,756,492 A | 5/1998 | Buelow et al. | |
| 8,563,605 B2 | 10/2013 | Miyanari et al. | |
| 8,617,802 B2 | 12/2013 | Köhl et al. | |
| 9,314,443 B2 * | 4/2016 | Rii ......... | A61K 31/22 |
| 9,399,029 B2 * | 7/2016 | Tanaka ................. | A61K 31/197 |
| 2004/0235162 A1 | 11/2004 | Sato | |
| 2005/0032210 A1 | 2/2005 | Sato et al. | |
| 2010/0061965 A1 | 3/2010 | Connolly et al. | |
| 2011/0196033 A1 | 8/2011 | Tanaka | |
| 2012/0213808 A1 | 8/2012 | Murakami et al. | |
| 2013/0052734 A1 | 2/2013 | Todo et al. | |
| 2013/0108710 A1 | 5/2013 | Tanaka et al. | |
| 2014/0188034 A1 | 7/2014 | Tanaka et al. | |
| 2014/0249217 A1 | 9/2014 | Rii et al. | |
| 2015/0174090 A1 | 6/2015 | Tanaka et al. | |

FOREIGN PATENT DOCUMENTS

| | | |
|---|---|---|
| EP | 1785132 A1 | 5/2007 |
| JP | 2000-191401 A | 7/2000 |
| JP | 2000-344602 A | 12/2000 |
| JP | 2002-060301 A | 2/2002 |
| JP | 2003-530101 A | 10/2003 |
| JP | 2004-298181 A | 10/2004 |
| JP | 2004-300098 A | 10/2004 |
| JP | 2005-508864 A | 4/2005 |
| JP | 2005-306749 A | 11/2005 |

(Continued)

OTHER PUBLICATIONS

Wood et al., "Regulatory T Cells in Transplantation Tolerance", Mar. 2003, Nature Reviews: Immunology, 3(3), pp. 199-210.*

(Continued)

*Primary Examiner* — My-Chau T. Tran
(74) *Attorney, Agent, or Firm* — Foley & Lardner LLP (57) ABSTRACT

The present invention provides an agent for promoting graft survival which can suppress rejection without use of existing immunosuppressants, an organ preservation solution capable of maintaining the freshness of an organ excised from a donor, and the like. An agent for promoting graft survival or an organ preservation solution is prepared, which comprises 5-aminolevulinic acid (ALA) or a derivative thereof, or a salt of ALA or the derivative and an iron compound as active ingredients. Preferable examples of the ALAs can include ALA and various esters such as methyl ester, ethyl ester, propyl ester, butyl ester, and pentyl ester of ALA, and their hydrochlorides, phosphates, and sulfates. Preferable examples of the iron compound can include sodium ferrous citrate.

16 Claims, 4 Drawing Sheets

(56) References Cited

FOREIGN PATENT DOCUMENTS

| | | |
|---|---|---|
| JP | 2006-069963 A | 3/2006 |
| JP | 2006-096745 A | 4/2006 |
| JP | 2006-290761 A | 10/2006 |
| JP | 2006-316000 A | 11/2006 |
| JP | 2007-131598 A | 5/2007 |
| JP | 2008-115089 A | 5/2008 |
| JP | 2009-143939 A | 7/2009 |
| JP | 2009-221128 A | 10/2009 |
| JP | 2009-298739 A | 12/2009 |
| JP | 4547174 B2 | 7/2010 |
| JP | 2011-016753 A | 1/2011 |
| JP | 2011-505378 A | 2/2011 |
| JP | 2011-522837 A | 8/2011 |
| WO | WO 95/02323 A1 | 1/1995 |
| WO | WO 01/77299 A2 | 10/2001 |
| WO | WO 02/098431 A1 | 12/2002 |
| WO | WO 2007/100154 A1 | 9/2007 |
| WO | WO 2009/073599 A1 | 6/2009 |
| WO | WO 2009/139156 A1 | 11/2009 |
| WO | WO 2009/149397 A2 | 12/2009 |
| WO | WO 2010/050179 A1 | 5/2010 |
| WO | WO 2011/048766 A1 | 4/2011 |
| WO | WO 2011/105394 A1 | 9/2011 |
| WO | WO 2011/145343 A1 | 11/2011 |
| WO | WO 2012/172821 A1 | 12/2012 |
| WO | WO 2013/054470 A1 | 4/2013 |

OTHER PUBLICATIONS

Wood et al., "Regulatory immune cells in transplantation", Jun. 2012, Nature Reviews: Immunology, 12(6), pp. 417-430.*

Juvet et al., "Harnessing Regulatory T Cells for Clinical Use in Transplantation: The End of the Beginning", Apr. 2014, American Journal of Transplantation, 14(4), pp. 750-763.*

Libetta et al., "Sirolimus vs cyclosporine after induction with basiliximab does not promote regulatory T cell expansion in de novo kidney transplantation: Results from a single-center randomized trial", 2015, Transplant Immunology, 33(2), pp. 117-124.*

Hou et al., "5-Aminolevulinic acidwithferrousironinduces permanent cardiac allograft acceptance in mice via induction of regulatory cells", 2015, The Journal of Heart and Lung Transplantation, 34(2), pp. 254-263.*

Fujino et al., "5-Aminolevulinic acid regulates the inflammatory response and alloimmune reaction", Aug. 2016, International Immunopharmacology, vol. 37, 71-78.*

Marino et al., "Allorecognition by T Lymphocytes and Allograft Rejection", Dec. 2016, Frontiers in Immunology, 7(582), pp. 1-9.*

Cai et al., "Carbon monoxide generated by 5-aminolevulinic acid results in cardiac allograft permanent acceptance by increasing regulatory T cell generation," Proceedings of the Japanese Society for Immunology, Nov. 2012, 41:55, 1-F-W10-7-O/P.

Corthay, A., "How do Regulatory T Cells Work?", Journal of Immunology, 2009, 70(4):326-336.

Egli et al., "Sensitivity of osteoblasts, fibroblasts, bone marrow cells, and dendritic cells to 5-aminolevulinic acid based photodynamic therapy," Journal of Photochemistry and Photobiology B: Biology, Nov. 2007, 89(2-3):70-77.

Evangelou et al., "Topical aminolaevulinic acid-photodynamic therapy produces an inflammatory infiltrate but reduces langerhans cells in healthy human skin in vivo," British Journal of Dermatology, 2011, 165(3):513-519.

Hayami et al., "Immunosuppression by Phtodynamic therapy," 27$^{th}$ Japanese Society for Photomedicine and Photobiology, Aug. 6-7, 2005, p. 61, with English translation.

Hayami et al., "Immunosuppressive effects of photodynamic therapy by topical aminolevulinic acid," Journal of Dermatology, 2007, 34:320-327.

Hryhorenko et al., "Antigen specific and nonspecific modulation of the immune response by aminolevulinic acid based photodynamic therapy," Immunopharmacology, 1998, 40(3):231-240.

Hryhorenko et al., "Deletion of Alloantigen-Activated Cells by Aminolevulinic Acid-Based Photodynamic Therapy," Photochemistry and Photobiology, Jan. 1, 1999, 69(5):560-565.

Iwata, Makoto, "Role of Retinoic acid in gut immunity," Chemistry and Biology, 2010, 48(6):389-394, with partial English Translation.

Matsushima et al., "Protective Effect of Coenzyme Q10 on Canine Myocardial Injury Caused by Ischemia and Reperfusion," Japanese Journal of Transplantation, 1990, 25(3):279-282, with English summary on first page.

Oellinger et al., "Role of heme oxygenase-1 in transplantation," Transplant International, 2010, 23(11):1071-1081.

Ran et al., "ALA-PDT allevieates graft-versus-host disease in mice following allogenic bone marrow transplantation," Chinese Journal of Contemporary Pediatrics, 2006, 8(5):408-412, with English abstract on first page.

Ran et al., "Effects of 5-aminolevulinic acid-mediated photodynamic therapy on GVHD and GVL following Allo-BMT in ALL mice," Journal of Clinical Pediatrics, 2007, 25(8):655-659.

Rocuts et al., "Bilirubin Promotes De Novo Generation of T Regulatory Cells," Cell Transplanation, 2010, 19(4):443-451.

Wachowska et al., "Aminolevulinic Acid (ALA) as a Prodrug in Photodynamic Therapy of Cancer," Molecules, May 19, 2011, 16:4140-4164.

Guibert et al., "Organ Preservation: Current Concepts and New Strategies for the Next Decade," Transfusion Medicine and Hemotherapy, Mar. 21, 2011, 38:125-142.

Latchana et al., "Preservation solutions used during abdominal transplantation: Current status and outcomes," World Journal of Transplantation, Dec. 24, 2015, 5(4):154-164.

Sakaguchi et al., "Regulatory T Cells and Immune Tolerance," Cell, May 30, 2008, 133:775-787.

* cited by examiner

Heart graft survival rate

[Figure 5]

Appearance of skin graft after 30 days

ENHANCER OF SURVIVAL OF TRANSPLANTED ORGAN

CROSS-REFERENCE TO RELATED APPLICATIONS

This application is a Divisional of U.S. application Ser. No. 14/350,488, which is the U.S. National Stage application of PCT/JP2012/005782, filed Sep. 12, 2012, which claims priority from Japanese application JP 2011-225384, filed Oct. 12, 2011 and JP 2012-157374, filed Jul. 13, 2012.

TECHNICAL FIELD

The present invention relates to an agent for promoting graft survival containing 5-aminolevulinic acid (hereinafter, also referred to as "ALA") or a derivative thereof, or a salt of ALA or the derivative and a metal-containing compound such as an iron compound, and an agent for preserving an organ excised from a donor comprising the agent for promoting graft survival, and the like.

BACKGROUND ART

Rejection after organ transplantation occurs when the immune system, which intrinsically defends the living body against bacteria, viruses, and so on, recognizes the graft as a "foreign substance". It is not an exaggeration to say that the success of medical transplantation hinges on how to take effective control of such rejection. The rejection control method reportedly includes a method involving locally controlling graft rejection and a method involving controlling systemic rejection response itself. The latter method is mainly practiced at present. The administration of calcineurin inhibitors (e.g., cyclosporin and tacrolimus) or steroidal drugs is widely carried out in order to suppress rejection after transplantation, but is also known to often cause adverse reactions.

In recent years, methods for artificially inducing immune tolerance have been developed for the purpose of reducing the doses of drugs. Such methods involve extracting T cells from donors or recipients, mixed-culturing the T cells with specific antibodies, and returning the resulting cells to their bodies. There have been proposed, for example: an agent for suppressing kidney transplantation rejection, containing recipient-derived T cells as an active ingredient, the T cells being obtained by collecting T cells from the recipient scheduled to receive kidney transplantation and stimulating the collected T cells with alloantigen from a kidney donor in the presence of an anti-CD80 antibody or its antigen-binding fragment and an anti-CD86 antibody or its antigen-binding fragment (see e.g., Patent Document 1); a method for reducing the influence of graft versus host disease, comprising the steps of: extracting, from a human donor, a sample comprising peripheral blood mononuclear cells comprising $CD4^+CD25^+$ regulatory T cells; concentrating the $CD4^+$ $CD25^+$ regulatory T cells in the sample to thereby form concentrated $CD4^+CD25^+$ regulatory T cells; proliferating the population of the concentrated $CD4^+CD25^+$ regulatory T cells; and administering a portion of the proliferated $CD4^+$ $CD25^+$ regulatory T cells to a human to treat the graft versus host disease (see e.g., Patent Document 2); and a method for inducing recipient cells so that rejection after transplantation is reduced, the method comprising a) isolating peripheral mononuclear blood cells from a recipient and a donor, b) mixing ex vivo the cells of the donor and the recipient, c) treating the resulting cells with a regulatory composition, d) increasing the number of the cells, and e) introducing the cells into the recipient (see e.g., Patent Document 3).

Other known techniques include: an organ preservation solution comprising flavonoid glycoside (see e.g., Patent Document 4); an agent for preserving an organ, containing 1,5-anhydrofructose or its derivative (see e.g., Patent Document 5); an agent for preserving an organ, containing fullerenes (see e.g., Patent Document 6); an organ preservation solution containing a hepatocyte growth factor (HGF) (see e.g., Patent Document 7); an organ preservation solution containing lecithinized superoxide dismutase (see e.g., Patent Document 8); and an agent for preserving an organ, comprising glucosyl-L-ascorbic acid or a salt thereof (see e.g., Patent Document 9).

Meanwhile, ALA is known as an intermediate in tetrapyrrole biosynthesis pathways present in a wide range of animals, plants, or bacteria. This acid is commonly biosynthesized from succinyl CoA and glycine by 5-aminolevulinic acid synthase. Photodynamic therapy using ALA (hereinafter, also referred to as "ALA-PDT") has also been developed and has received attention as a low invasive treatment method capable of maintaining QOL. For example, diagnostic or therapeutic agents for tumor comprising ALA and so on have been reported. In addition, ALA is also known to be useful as a preventing and improving agent or a therapeutic agent for adult disease, cancer, or male sterility (see e.g., Patent Documents 10 to 12).

PRIOR ART DOCUMENTS

Patent Documents

Patent Document 1: Japanese unexamined Patent Application Publication No. 2007-131598
Patent Document 2: Japanese unexamined Patent Application Publication (Translation of PCT Application) No. 2011-505378
Patent Document 3: Japanese unexamined Patent Application Publication (Translation of PCT Application) No. 2003-530101
Patent Document 4: Japanese unexamined Patent Application Publication No. 2009-221128
Patent Document 5: Japanese unexamined Patent Application Publication No. 2008-115089
Patent Document 6: Japanese unexamined Patent Application Publication No. 2006-316000
Patent Document 7: Japanese unexamined Patent Application Publication No. 2005-306749
Patent Document 8: Japanese unexamined Patent Application Publication No. 2002-60301
Patent Document 9: Japanese unexamined Patent Application Publication No. 2000-191401
Patent Document 10: International Publication No. WO2010/050179
Patent Document 11: Japanese unexamined Patent Application Publication No. 2011-16753
Patent Document 12: International Publication No. WO2009/139156

SUMMARY OF THE INVENTION

Object to be Solved by the Invention

Reportedly, the long-term dosing of immunosuppressants is required for preventing rejection, which is most responsible for the failure of graft functions after transplantation. The long-term administration of immunosuppressants, however, might cause serious adverse reactions such as infections, renal damage, diabetes mellitus, lymphoid hyperplasia, malignant tumors, and cardiovascular complications and must be strictly controlled. The method for artificially inducing immune tolerance, involving, for example, extracting T cells, mixed-culturing the T cells with specific antibodies, and returning the resulting cells to the bodies, has not yet been widespread due to its complicated procedures resulting from several weeks necessary for the cell culture period and observed adverse reactions such as alopecia, though this method can reduce the dose of immunosuppressants. Various other tolerance induction systems have been experimentally developed, but have hardly been put in actual clinical application.

An object of the present invention is to provide a safe agent for promoting graft survival which can promote graft survival after organ transplantation under the mechanism of action different from that of conventional drugs, an organ preservation solution capable of maintaining the freshness of an organ excised from a donor, or the like.

Means to Solve the Object

The present inventors have continued various studies on the medical application of ALA. In the course of study on the suppression of rejection after organ transplantation, the present inventors have found that ALA has a graft survival-promoting effect. Also, the present inventors have adventitiously found that when a composition containing ALA alone or ALAs in combination with an iron compound is administered to a donor prior to transplantation surgery and also administered to a recipient that has received the transplantation of an organ excised from the donor, the graft survival rate increases significantly, while immunosuppressants used in conventional organ transplantation were administered only to a recipient. The present inventors have further found that spleen cells of the organ-transplanted recipient are administered to another recipient at the same time with the transplantation of an organ excised from a donor thereby bring about a secondary immune tolerance inducing effect so that graft survival is promoted even without the administration of ALA. The present inventors have further found that ALA is effective as an agent for preserving an organ excised from a donor.

In addition, the present inventors have found that an iron compound collaborates with ALA to potentiate a graft survival-promoting effect, a secondary immune tolerance inducing effect, and an effect of maintaining the freshness of an organ excised from a donor. The administration of ALA alone may suffice in the presence of the abundant iron compound or in the case where the iron compound is separately taken. Among minerals, iron is often lacking in Japanese, who take a smaller amount of lean meat than foreign people. For this reason, ALA was added together with the iron compound in some Examples directed to Japanese. This is not necessary in the case where the subject is a person with sufficient iron storage. Also, ALA is widely known to be metabolized into porphyrin, which exhibits PDT or PDD activity upon light irradiation. The agent for promoting graft survival of the present invention does not require light.

The present inventors have further conducted diligent studies on administration methods and doses and consequently established an agent for promoting graft survival, comprising ALAs alone, or ALAs and an iron compound as active ingredients. Based on these findings, the present invention has been completed.

Specifically, the present invention relates to:
(1) an agent for promoting graft survival, containing a compound represented by the following formula (I) or a salt thereof:

(wherein $R^1$ represents a hydrogen atom or an acyl group; and $R^2$ represents a hydrogen atom, a linear or branched alkyl group, a cycloalkyl group, an aralkyl group, or an aryl group);
(2) the agent for promoting graft survival according to (1), wherein $R^1$ and $R^2$ each represent a hydrogen atom;
(3) the agent for promoting graft survival according to (1) or (2), further containing an iron compound;
(4) the agent for promoting graft survival according to (3), wherein the iron compound is one or more compound(s) selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide;
(5) the agent for promoting graft survival according to (3), wherein the iron compound is sodium ferrous citrate;
(6) a method for promoting graft survival after organ transplantation, comprising administering an agent for promoting graft survival according to any one of (1) to (5) to a recipient before and/or after organ transplantation;
(7) a method for promoting graft survival after organ transplantation, comprising administering an agent for promoting graft survival according to any one of (1) to (5) to a donor before organ transplantation and to a recipient before and/or after organ transplantation;
(8) a kit for promoting graft survival, comprising: a) a compound represented by the formula (I) or a salt thereof; and b) an iron compound;
(9) a method for promoting graft survival, comprising administering a) a compound represented by the formula (I) or a salt thereof and b) an iron compound at the same time or in tandem to a subject;
(10) a combination for an agent for promoting graft survival, comprising: a) a compound represented by the formula (I) or a salt thereof; b) an iron compound; and c) an immunosuppressant for organ transplantation;
(11) a combination for an agent for promoting graft survival, comprising: a) an agent for promoting graft survival according to any one of (1) to (5); and b) an immunosuppressant for organ transplantation;
(12) an isolated immunocyte derived from a recipient, wherein an agent for promoting graft survival according to any one of (1) to (5) has been administered to the recipient before and/or after organ transplantation;

(13) an isolated immunocyte derived from a recipient, wherein an agent for promoting graft survival according to any one of (1) to (5) has been administered to a donor before organ transplantation and to the recipient before and/or after organ transplantation;
(14) the isolated immunocyte according to (12) or (13), wherein the immunocyte is a regulatory T cell;
(15) a method for secondary immune tolerance induction, comprising administering an immunocyte according to any one of (12) to (14) to a recipient identical with and/or a recipient different from the origin of the immunocyte;
(16) a method for preserving an organ for transplantation, comprising administering an agent for promoting graft survival according to any one of (1) to (5) to an organ excised from a donor or a preservation solution for the organ;
(17) the preservation method according to (16), wherein the organ is derived from a donor to which the agent for promoting graft survival according to any one of (1) to (5) has been administered in advance before organ transplantation;
(18) an agent for preserving an organ excised from a donor, comprising an agent for promoting graft survival according to any one of (1) to (5);
(19) a compound represented by the formula (I) or a salt thereof for use in improvement in graft survival rate;
(20) a compound represented by the formula (I) or a salt thereof and an iron compound for use in improvement in graft survival rate;
(21) use of a compound represented by the formula (I) or a salt thereof for the production of an agent for promoting graft survival;
(22) use of a compound represented by the formula (I) or a salt thereof and an iron compound for the production of an agent for promoting graft survival;
(23) a compound represented by the formula (I) or a salt thereof for use in an agent for preserving an organ excised from a donor;
(24) a compound represented by the formula (I) or a salt thereof and an iron compound for use in an agent for preserving an organ excised from a donor;
(25) use of a compound represented by the formula (I) or a salt thereof for the production of an agent for preserving an organ excised from a donor; and
(26) use of a compound represented by the formula (I) or a salt thereof and an iron compound for the production of an agent for preserving an organ excised from a donor.

Effect of the Invention

The agent for promoting graft survival of the present invention can defend a graft against stress, maintain its freshness, suppress rejection associated with organ transplantation, and enhance the graft survival rate. The agent of the present invention totally differs in mechanism from existing immunosuppressants or the method for artificially inducing immune tolerance, involving, for example, extracting T cells, mixed-culturing the T cells with specific antibodies, and returning the resulting cells to the bodies, and is very effective as an agent for promoting graft survival after organ transplantation which hardly causes adverse reactions and eliminates the need of long-term dosing of drugs. In addition, the agent of the present invention differs in the action mechanism from conventional immunosuppressants or the like and is thus expected to enhance effects by combined use with existing drugs. The agent for preserving an organ of the present invention can maintain the freshness of an organ excised from a donor.

MODE OF CARRYING OUT THE INVENTION

The agent for promoting graft survival of the present invention is not particularly limited as long as the agent comprises a compound represented by the formula (I) or a salt thereof (hereinafter, they are also collectively referred to as "ALAs") as an active ingredient. For the agent for promoting graft survival of the present invention, it is preferred to contain an iron compound in addition to ALAs. The agent for promoting graft survival of the present invention, particularly, the agent for promoting graft survival, containing ALAs and an iron compound, can be administered to a subject including humans as well as livestock/fowl or pets to thereby promote graft survival after organ transplantation. In the present invention, the promotion of graft survival refers to enhancement in a survival rate at which rejection after organ transplantation (including tissue transplantation) is suppressed so that the graft (transplanted organ or tissue) continues functioning in the living body.

The kit for promoting graft survival of the present invention is not particularly limited as long as the kit comprises ALAs and an iron compound (as individual drugs) as active ingredients. Use of the kit for promoting graft survival can promote graft survival after organ transplantation into a subject including humans as well as livestock/fowl or pets. The kit for promoting graft survival may further comprise a package insert such as an instruction manual.

The organ to be transplanted is not particularly limited as long as the organ can be transplanted. The organ may be not only an organ excised from a donor but a graft or cells prepared in vitro or a tissue/organ artificially constructed by regenerative medical techniques or may further be an organ or the like prepared from embryonic stem cells. Examples of the type of the organ can include the kidney, the liver, the heart, the pancreas, the lung, the small intestine, eyeballs, the cornea, the hair, and the skin. Among them, preferable examples thereof can include the kidney, the liver, the heart, the pancreas, the lung, and the small intestine.

The combination for an agent for promoting graft survival of the present invention is not particularly limited as long as the combination comprises the agent for promoting graft survival of the present invention and an immunosuppressant for organ transplantation or comprises ALAs, an iron compound, and an immunosuppressant for organ transplantation. The administration of these combinations can promote graft survival. Examples of the immunosuppressant for organ transplantation can include pharmaceuticals such as: antimetabolites such as azathioprine, mercaptopurine, methotrexate, mycophenolic acid, and leflunomide; alkylating agents such as cyclophosphamide; calcineurin inhibitors such as cyclosporin and tacrolimus; and steroids. The agent for promoting graft survival and the kit for promoting graft survival of the present invention differ in the mechanism of action from existing immunosuppressants for organ transplantation. Thus, use of the combination for an agent for promoting graft survival of the present invention can be expected to produce additive effects and, in some cases, synergistic effects.

Examples of the compound used as an active ingredient in the agent for promoting graft survival of the present invention can include a compound represented by the formula (I) or a salt thereof (hereinafter, they are also collectively referred to as "ALAs"). ALA, also called δ-aminolevulinic acid, is represented by the formula (I) wherein $R^1$ and $R^2$ each represent a hydrogen atom, and is one type of amino acid. Examples of ALA derivatives can include compounds (other than ALA) represented by the formula (I) wherein $R^1$ represents a hydrogen atom or an acyl group; and $R^2$ represents a hydrogen atom, a linear or branched alkyl group, a cycloalkyl group, an aryl group, or an aralkyl group.

Among these ALAs, preferable examples thereof include ALA represented by the formula (I) wherein $R^1$ and $R^2$ each represent a hydrogen atom or a salt thereof. ALA, also called δ-aminolevulinic acid, is one type of amino acid. Examples of ALA derivatives can include compounds (other than ALA) represented by the formula (I) wherein $R^1$ represents a hydrogen atom or an acyl group; and $R^2$ represents a hydrogen atom, a linear or branched alkyl group, a cycloalkyl group, an aryl group, or an aralkyl group.

Examples of the acyl group in the formula (I) can include: linear or branched alkanoyl groups having 1 to 8 carbon atoms such as formyl, acetyl, propionyl, butyryl, isobutyryl, valeryl, isovaleryl, pivaloyl, hexanoyl, octanoyl, and benzylcarbonyl groups; and aroyl groups having 7 to 14 carbon atoms such as benzoyl, 1-naphthoyl, and 2-naphthoyl groups.

Examples of the alkyl group in the formula (I) can include linear or branched alkyl groups having 1 to 8 carbon atoms such as methyl, ethyl, propyl, isopropyl, butyl, isobutyl, sec-butyl, tert-butyl, pentyl, isopentyl, neopentyl, hexyl, heptyl, and octyl groups.

Examples of the cycloalkyl group in the formula (I) can include cycloalkyl groups having 3 to 8 carbon atoms which are saturated or may have a partially unsaturated bond, such as cyclopropyl, cyclobutyl, cyclopentyl, cyclohexyl, cycloheptyl, cyclooctyl, cyclododecyl, and 1-cyclohexenyl groups.

Examples of the aryl group in the formula (I) can include aryl groups having 6 to 14 carbon atoms such as phenyl, naphthyl, anthryl, and phenanthryl groups.

Examples of the aralkyl group in the formula (I) can include aralkyl groups whose aryl moiety is the same as those exemplified above as the aryl group and alkyl moiety is the same as those exemplified above as the alkyl group and can specifically include aralkyl groups having 7 to 15 carbon atoms such as benzyl, phenethyl, phenylpropyl, phenylbutyl, benzhydryl, trityl, naphthylmethyl, and naphthylethyl groups.

The ALA derivative is preferably a compound wherein $R^1$ is, for example, a formyl, acetyl, propionyl, or butyryl group or a compound wherein $R^2$ is, for example, a methyl, ethyl, propyl, butyl, or pentyl group. Preferable examples of combinations of $R^1$ and $R^2$ can include combinations of formyl and methyl, acetyl and methyl, propionyl and methyl, butyryl and methyl, formyl and ethyl, acetyl and ethyl, propionyl and ethyl, and butyryl and ethyl.

It is only required that ALAs should act as an active ingredient in the form of ALA of the formula (I) or its derivative in vivo. ALAs can be administered as various salts, esters, or prodrugs (precursors), which are degradable by enzymes in vivo, in order to enhance solubility according to dosage forms. Examples of the salts of ALA and its derivative can include pharmacologically acceptable acid-addition salts, metal salts, ammonium salts, and organic amine-addition salts. Examples of the acid-addition salts can include: various inorganic acid salts such as hydrochloride, hydrobromide, hydroiodide, phosphate, nitrate, and sulfate; and various organic acid-addition salts such as formate, acetate, propionate, toluenesulfonate, succinate, oxalate, lactate, tartrate, glycolate, methanesulfonate, butyrate, valerate, citrate, fumarate, maleate, and malate. Examples of the metal salts can include: various alkali metal salts such as lithium salt, sodium salt, and potassium salt; various alkaline earth metal salts such as magnesium salt and calcium salts; and salts of various other metals such as aluminum and zinc. Examples of the ammonium salts can include ammonium salt and alkylammonium salts such as tetramethylammonium salts. Examples of the organic amine salts can include various salts such as triethylamine salt, piperidine salt, morpholine salt, and toluidine salt. These salts may be used in the form of solution.

Of these ALAs, ALA and various esters thereof such as ALA methyl ester, ALA ethyl ester, ALA propyl ester, ALA butyl ester, and ALA pentyl ester, and their hydrochlorides, phosphates, and sulfates are desirable. Particularly preferable examples thereof can include ALA hydrochloride and ALA phosphate.

These ALAs can be produced by any method known in the art such as chemical synthesis, microbial production, or enzymatic production. Also, these ALAs may form a hydrate or a solvate and can be used alone or in appropriate combination of two or more thereof.

The iron compound may be an organic salt or an inorganic salt. Examples of the inorganic salt can include ferric chloride, iron sesquioxide, iron sulfate, and ferrous pyrophosphate. Examples of the organic salt can include: carboxylates, for example, hydroxycarboxylates including citrates such as ferrous citrate, iron sodium citrate, sodium ferrous citrate, and iron ammonium citrate; organic acid salts such as ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, and sodium iron succinate citrate; and heme iron, iron dextran, iron triethylenetetramine, lactoferrin iron, transferrin iron, sodium iron chlorophyllin, ferritin iron, saccharated iron oxide, and iron glycine sulfide. Among them, sodium ferrous citrate or iron sodium citrate is preferable.

These iron compounds may be used alone or as a mixture of two or more thereof. The dose of the iron compound can be 0.01 to 100-fold in molar ratio with respect to the dose of ALAs (in terms ALA) and is preferably 0.05 to 10-fold, more preferably 0.1 to 8-fold with respect to the dose of ALAs (in terms of ALA).

The agent for promoting graft survival of the present invention may further contain other metal compounds within a range that does not cause an excess, instead of or in addition to the iron compound. Examples of the metal compounds can include magnesium compounds, zinc compounds, nickel compounds, vanadium compounds, cobalt compounds, copper compounds, chromium compounds, and molybdenum compounds.

For the method for promoting graft survival of the present invention, it is preferred to administer ALAs and an iron compound in combination. In this case, ALAs and the iron compound can be administered either as a composition comprising them or each independently at the same time or in tandem. In the case where ALAs and the iron compound are administered each independently, it is preferred to administer them at the same time. In the case where ALAs and the iron compound are administered each independently in tandem, it is preferred to administer them so as to produce additive effects, preferably synergistic effects.

The agent for promoting graft survival of the present invention may be administered only to a recipient after transplantation of, for example, an organ excised from a donor, an organ temporarily stored in a preservation solution after its excision from a donor, an organ prepared for autologous transplantation using regenerative medical techniques, or any of these organs dipped in ALAs. It is preferred to also administer the agent to a donor before organ excision, because of improving the survival rate. Thus, a big feature of the present invention is that the agent for promoting graft survival or the kit for promoting graft survival of the present invention can be administered to a donor before organ transplantation and to a recipient after organ transplantation or before and after transplantation to thereby improve the survival rate.

An isolated immunocyte derived from a recipient, wherein the agent for promoting graft survival or the kit for promoting graft survival of the present invention has been administered to the recipient before and/or after organ transplantation, or an isolated immunocyte derived from a recipient, wherein the agent for promoting graft survival or the kit for promoting graft survival of the present invention has been administered to a donor before organ transplantation and to the recipient before and/or after organ transplantation, can be proliferated, if necessary, and administered to the recipient identical with and/or a recipient different from the origin of the immunocyte. As a result, immune tolerance induction is promoted (promotion of secondary induction of immune tolerance) in the immunocyte-administered recipient at an individual level even without the administration of the agent for promoting graft survival or the kit for promoting graft survival of the present invention. This promotion of secondary induction of immune tolerance shows that the promotion of graft survival is based on induced immune tolerance. This approach can be applied to adoptive immunotherapy. Provided that, for example, immunocytes are taken out of a human with induced immune tolerance and temporarily stored, these cells can be transplanted when immune tolerance is cancelled (e.g., a graft is rejected), to thereby recover the state of immune tolerance even without the administration of the agent for promoting graft survival of the present invention. A particularly big feature of the present invention is this promotion of secondary induction of immune tolerance.

Examples of the immunocyte can include spleen cells as well as macrophages, dendritic cells, T cells, B cells, NK cells, neutrophils, eosinophils, and myeloid-derived suppressor cells (MDSCs). Regulatory T cells or spleen cells are preferable.

Examples of administration routes for each ingredient in the agent for promoting graft survival or the kit for promoting graft survival of the present invention can include oral administration (including sublingual administration) and parenteral administration such as nasal drip, inhalation, intravenous administration (including drip infusion), transdermal administration using patches or the like, and administration based on suppositories or forced enteral feeding using nasogastric tubes, nasoenteric tubes, gastric fistula tubes, or intestinal fistula tubes. Oral administration is preferable.

The dosage form of each ingredient in the agent for promoting graft survival or the kit for promoting graft survival of the present invention can be appropriately determined according to the administration route. Examples thereof can include injections, nasal drops, intravenous drops, tablets, capsules, fine granules, powders, solutions, liquid agents dissolved in syrups or the like, patches, and suppositories. Each ingredient in the agent for promoting graft survival or the kit for promoting graft survival of the present invention may be administered for medical use as well as in the form of supplement tablets or capsules. Particularly, the form of disintegrating tablets that are rapidly disintegrable in the mouth or the form of solutions suitable for nasogastric administration is preferable for elderly people, infants, or the like who have difficulty in swallowing.

The agent for promoting graft survival or the kit for promoting graft survival of the present invention can be prepared, if necessary, by the addition of pharmacologically acceptable carriers, excipients, diluents, additives, disintegrants, binders, coating agents, lubricants, glidants, flow conditioners, flavoring agents, sweetening agents, solubilizers, solvents, gelling agents, nutrients, etc. Specific examples thereof can include water, saline, animal fat and oil, plant oil, lactose, starch, gelatin, crystalline cellulose, gum, talc, magnesium stearate, hydroxypropylcellulose, polyalkylene glycol, polyvinyl alcohol, and glycerin. In the case of preparing the agent for promoting graft survival or the kit for promoting graft survival of the present invention as an aqueous solution, it should be noted that the aqueous solution is kept from becoming alkaline, in order to prevent the degradation of ALAs. If the aqueous solution becomes alkaline, the degradation of ALAs may be prevented by the removal of oxygen.

The agent for promoting graft survival of the present invention is useful in suppressing immune response in a recipient evoked by the transplantation of an organ excised from a donor into the recipient, suppressing rejection associated with such organ transplantation, and enhancing the graft survival rate and thus, can be used as an agent for preserving an organ excised from a donor. In addition, the agent for promoting graft survival of the present invention can be added to existing organ preservation solutions to thereby potentiate an effect of promoting graft survival after organ transplantation. Examples of the rejection can include hyperacute rejection, acute rejection, and chronic rejection after organ transplantation.

The hyperacute rejection is often seen in heterologous organ transplantation and defined as strong rejection that occurs from immediately to within 24 hours after transplantation. The presence or absence of the hyperacute rejection can be determined on the basis of, for example, whether or not a thrombus is formed in the artery of the graft within several minutes to several hours after blood reflow in the sutured vessel. In the case of heart transplantation, the presence or absence of the hyperacute rejection can be determined on the basis of the stop of beating from immediately to within 24 hours after transplantation. The acute rejection is defined as rejection that occurs between 3 days and around 1 week after transplantation. In the case of heart transplantation, the presence or absence of the acute rejection can be determined on the basis of the stop of beating at or beyond 24 hours after transplantation. The chronic rejection is defined as rejection that occurs at or beyond 3 months after transplantation. In the case of heart transplantation, the presence or absence of the chronic rejection may be determined on the basis of the stop of beating, though the detailed mechanism of the chronic rejection is unknown.

Examples of the donor and/or the recipient according to the present invention can include mammals such as humans, baboon, cattle, pigs, dogs, cats, rabbits, rats, and mice. The aspect of organ transplantation performed using the agent for promoting graft survival of the present invention is not particularly limited as long as an organ can be transplanted from the donor to the recipient according to this aspect. Examples thereof can include: homologous organ transplantation from mice to mice, from rats to rats, from rabbits to rabbits, from dogs to dogs, from cats to cats, from pigs to pigs, from monkeys to monkeys, from baboon to baboon, or from humans to humans; and heterologous organ transplantation from pigs to humans, from cattle to humans, from monkeys to humans, from baboon to humans.

The organ transplantation using the agent for promoting graft survival of the present invention can be performed according to a routine method. The organ transplantation may be orthotopic organ transplantation in which an organ provided from a donor or the like is transplanted into the corresponding site of a recipient from which the organ has been removed, or may be heterotopic organ transplantation in which an organ provided from a donor or the like is transplanted into a site different from the corresponding site in a recipient with the organ unremoved.

The agent for promoting graft survival of the present invention needs to be administered to an organ-transplanted recipient. Examples of the specific time of administration can include a period from a day after the transplantation date to 10 days later, preferably from a day after the transplantation date to 15 days later, more preferably from a day after the transplantation date to 1 month later, particularly preferably from a day after the transplantation date to a day when graft survival is sufficiently confirmed. The agent for promoting graft survival of the present invention may be administered for a longer period, if necessary, and can also be administered since before the transplantation date.

For improving the survival rate, it is preferred, as described above, that the agent for promoting graft survival of the present invention should be administered in advance to a donor from which an organ is excised. However, in the case of, particularly, brain-dead transplantation or the like which cannot afford to administer a sufficient amount of the agent to a donor, the agent may be administered directly to an organ excised from the donor, or the organ may be dipped in a solution containing the agent for promoting graft survival of the present invention. Alternatively, the agent for promoting graft survival of the present invention may be added into a storage solution containing the organ. Such administration to the excised organ also produces similar effects. This approach of adding the agent into the organ storage solution can also be adopted for use of an organ prepared for autologous transplantation by regenerative medical techniques. Thus, the agent for preserving an organ excised from a donor of the present invention comprises the agent for promoting graft survival and can be constructed as a solid type (e.g., powders, granules, or tablets) or a liquid type. The solid type can be supplemented, if necessary, with a dispersant, a solubilizer, and a pH adjuster. For the liquid type, it is preferred to have a buffering capacity. Also, the liquid type may be in the form of a concentrated preservation solution and diluted with saline or the like in use.

For administering the agent for promoting graft survival of the present invention to the donor according to the present invention, it is required to administer the agent for the predetermined period before organ excision. Examples of the specific time of administration can include a period from 1 week before the operation date for organ excision to the excision date, preferably from 5 days before the excision date to the excision date, more preferably from 3 days before the excision date to the excision date, further preferably from 2 days before the excision date to the excision date. In the case where, for example, an organ must be transported after its excision operation, it is preferred to take measures such as the storage of the agent for promoting graft survival of the present invention in the preservation solution.

The agent for promoting graft survival or the kit for promoting graft survival of the present invention can also be used, as described above, for humans as well as in the veterinary field including livestock/fowl or pets. The dose, administration frequency, and administration period of the agent for promoting graft survival or the like differ depending on the age, body weight, conditions, etc., of, for example, a human subject. Examples of the dose of ALAs per adult can include 0.1 to 12 mmol/day, preferably 0.2 to 9 mmol/day, more preferably 0.3 to 6 mmol/day, further preferably 0.35 mmol/day to 4 mmol/day in terms of moles of ALA. Examples of the administration frequency can include one or more dosages per day and continuous administration using drip infusion or the like. The administration period may be determined by a pharmacologist in this technical field or a clinician according to existing methods.

Examples of the concentration of ALAs in the agent for promoting graft survival of the present invention, used as an organ preservation solution, can include 0.1 µM to 100 mM. The concentration is preferably 1 µM to 10 mM, more preferably 5 µM to 5 mM, most preferably 10 µM to 1 mM.

The agent for promoting graft survival of the present invention may be used in combination with other existing immunosuppression methods for organ transplantation. Examples of the existing immunosuppression methods for organ transplantation can include methods for inducing immune tolerance using immunosuppressive monoclonal antibodies such as antibodies against CD2, CD3, CD4, CD7, CD25, CD28, CD45, or B7. Since the mechanism underlying the immunosuppressive effect of ALA on organ transplantation may fundamentally differ from the respective mechanisms of these drugs or methods, such combined use can be expected to produce additive effects and, in some cases, synergistic effects. In addition, the effect of reducing adverse reactions can also be expected because the agent for promoting graft survival of the present invention can decrease the dose of existing immunosuppressants for organ transplantation.

Hereinafter, the present invention will be described more specifically with reference to Examples. However, the technical scope of the present invention is not intended to be limited to these examples.

EXAMPLE 1

[Preparation of Heterotopic Homologous Heart-transplanted Model Mice]

B10 mice (male, 10 weeks old on average, body weight: 20 to 25 g) were used as donors for the hearts to be transplanted. CBA mice (male, 10 weeks old on average, body weight: 20 to 25 g) were used as recipients to receive the hearts taken out of the donors. The procedures of the heterotopic homologous heart transplantation in mice followed the description of Experimental Manual of Organ Transplantation (Shujunsha Co., Ltd.), Paragraph 1, Part 2, 2-1-5 "Heterotopic Heart Transplantation in Mice". Hereinafter, the procedures will be summarized.

The thorax of each donor mouse was opened under anesthesia and sufficiently perfused using 1 mL of saline supplemented with cold heparin, followed by excision of the heart. The excised heart was preserved in saline supplemented with cold heparin. The abdomen of each recipient mouse was opened under anesthesia, and the heart excised from the donor mouse was transplanted into the abdominal vena cava to prepare heterotopic heart-transplanted model mice.

EXAMPLE 2

[Homologous Heart Graft Survival Efficiency in Mice (1)]

Figure 1:
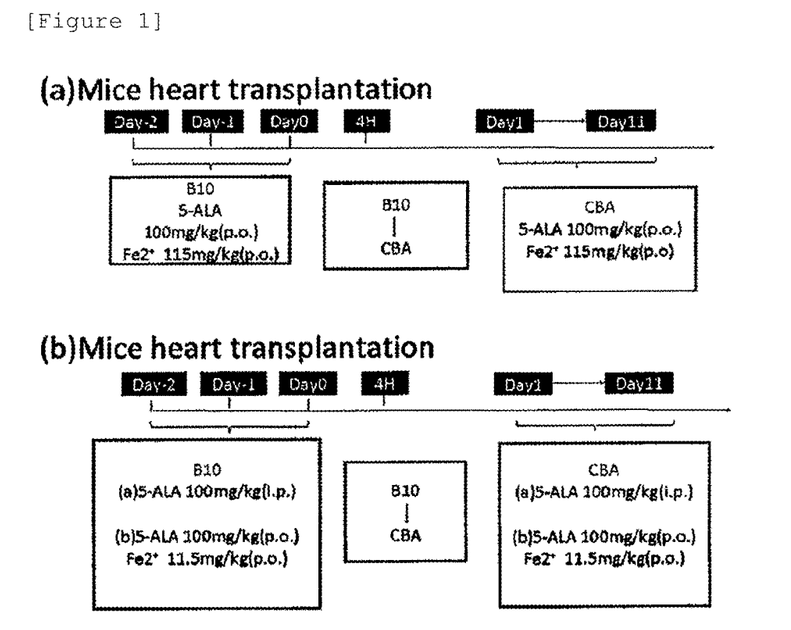
FIG. 1 shows an exemplary diagram of an experiment on heart transplantation between mice of different strains.

The heterotopic heart-transplanted model mice were divided into groups (1) to (4) with administration patterns shown in Table 1 below. An experiment was conducted on the oral administration of the agent for promoting graft survival of the present invention. The test mice took the administration composition and were additionally permitted to freely take diets or water before anesthesia and after recovering from anesthesia. The experiment is summarized in FIG. 1.

TABLE 1

| | Mice in administration | Administration composition | Administration period |
| --- | --- | --- | --- |
| Group (1) Control n = 6 | Donor mice + Recipient mice | Sterilized water Sterilized water | From 2 days before excision to excision date From day after transplantation to 11th day |
| Group (2) n = 6 | Donor mice Recipient mice | ALA phosphate 100 mg/kg Sodium ferrous citrate 115 mg/kg Sterilized water | From 2 days before excision to excision date From day after transplantation to 11th day |
| Group (3) n = 4 | Donor mice Recipient mice | Sterilized water ALA phosphate 100 mg/kg Sodium ferrous citrate 115 mg/kg | From 2 days before excision to excision date From day after transplantation to 11th day |
| Group (4) n = 7 | Donor mice Recipient mice | ALA phosphate 100 mg/kg Sodium ferrous citrate 115 mg/kg ALA phosphate 100 mg/kg Sodium ferrous citrate 115 mg/kg | From 2 days before excision to excision date From day after transplantation to 11th day |

Figure 2:
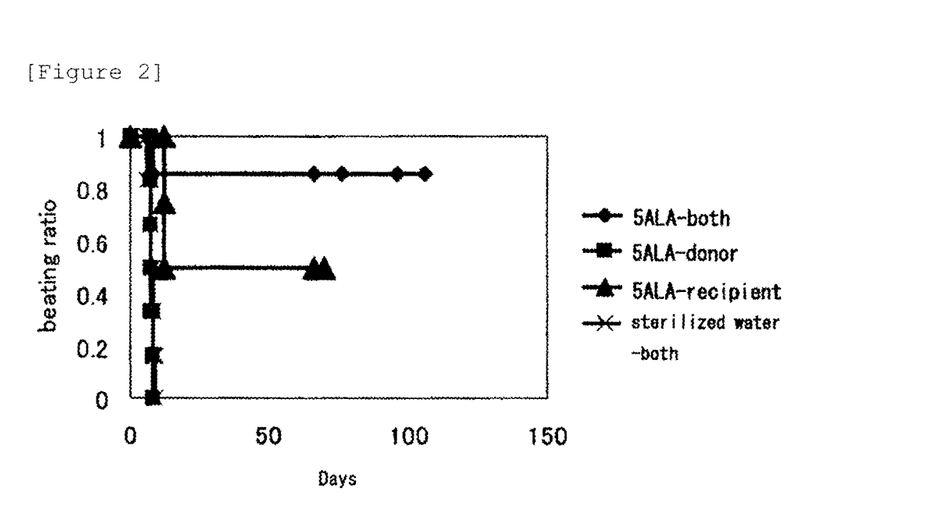
FIG. 2 is a diagram showing the summary of heart transplantation between mice of different strains using the agent for promoting graft survival of the present invention and a post-transplantation course. The ordinate denotes a heart beating rate.

The results of administration to groups (1) to (4) are shown below. Also, the relationship between the number of days elapsed and a heart beating rate is shown in FIG. 2.

The hearts transplanted in all individuals in group (1) in which both the donor and recipient mice received sterilized water stopped beating up to the 9th day. Long-term beating was seen in none of these individuals. More specifically, each heart graft stopped beating in one mouse on the 6th day after transplantation, in two mice on the 7th day, in two mice on the 8th day, and in one mouse on the 9th day.

The hearts transplanted in all individuals in group (2) in which only the donor mice received ALA (100 mg/kg)+SFC (115 mg/kg) stopped beating, or they died up to the 8th day. Long-term beating was seen in none of these individuals. Each heart graft stopped beating in four mice on the 7th day and in two mice on the 8th day.

Long-term beating was found in some individuals in group (3) in which only the recipient mice received ALA (100 mg/kg)+SFC (115 mg/kg). More specifically, each heart graft stopped beating in two mice on the 12th day. The heart graft in one individual still beat when 66 days had passed, and the heart graft in one individual still beat when 70 days had passed.

The heart grafts were confirmed to continue long-term beating in a significantly large number of individuals in group (4) in which both the donor and recipient mice received ALA (100 mg/kg)+SFC (115 mg/kg). More specifically, the heart graft stopped beating in one mouse on the 8th day. The heart grafts in two individuals still beat when 66 days had passed and when 76 days had passed, and the heart graft in one individual still beat when 96 days had passed and when 106 days had passed.

Since this experimental model underwent highly invasive surgery, it was reasonably anticipated that some individuals would die of stress independently of the presence or absence of administration of ALAs and an iron compound. Nevertheless, the oral administration of ALAs and the iron compound to donors before transplantation and to recipients after transplantation resulted in a large number of individuals whose heart graft continued long-term beating, demonstrating that the administration of ALAs and the iron compound remarkably enhanced the graft survival rate. Long-term beating was also found in some mice of group (3), demonstrating that the agent for promoting graft survival of the present invention was effective even when administered only to recipients after transplantation.

[Homologous Heart Graft Survival Efficiency in Mice (2)]

The heterotopic homologous heart-transplanted model mice were divided into groups (a) to (e) with administration patterns shown in Table 2 below. The agent for promoting graft survival of the present invention was studied for difference in effect depending on the content of the iron compound. The test mice took the administration composition and were additionally permitted to freely take diets or water before anesthesia and after recovering from anesthesia.

TABLE 2

| | Mice in administration | Administration composition | Administration period |
|---|---|---|---|
| Group (a) Control n = 9 | Donor mice + | Sterilized water | From 2 days before excision to excision date |
| | Recipient mice | Sterilized water | From day after transplantation to 11th day |
| Group (b) n = 5 | Donor mice | ALA phosphate 100 mg/kg | From 2 days before excision to excision date |
| | Recipient mice | ALA phosphate 100 mg/kg | From day after transplantation to 11th day |
| Group (c) n = 5 | Donor mice | ALA phosphate 100 mg/kg Sodium ferrous citrate 11.5 mg/kg | From 2 days before excision to excision date |
| | Recipient mice | ALA phosphate 100 mg/kg Sodium ferrous citrate 11.5 mg/kg | From day after transplantation to 11th day |
| Group (d) n = 6 | Donor mice | ALA phosphate 100 mg/kg Sodium ferrous citrate 115 mg/kg | From 2 days before excision to excision date |
| | Recipient mice | ALA phosphate 100 mg/kg Sodium ferrous citrate 115 mg/kg | From day after transplantation to 11th day |
| Group (e) n = 3 | Donor mice | Sterilized water | From 2 days before excision to excision date |
| | Recipient mice | ALA phosphate 100 mg/kg Sodium ferrous citrate 11.5 mg/kg | From day after transplantation to 11th day |

Figure 3:
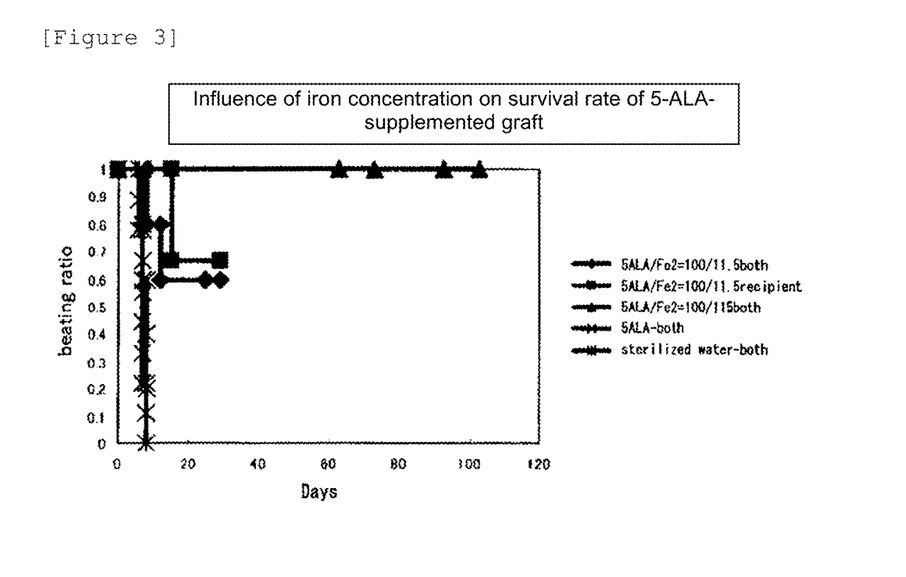
FIG. 3 is a diagram showing the summary of heart transplantation between mice of different strains according to another aspect using the agent for promoting graft survival of the present invention and a post-transplantation course. The ordinate denotes a heart beating rate.

The results of administration to groups (a) to (e) are shown below. Also, the relationship between the number of days elapsed and a heart beating rate is shown in FIG. 3.

The hearts transplanted in all individuals in group (a) in which both the donor and recipient mice received sterilized water stopped beating up to the 9th day. Long-term beating was seen in none of these individuals. More specifically, each heart graft stopped beating in two mice on the 6th day after transplantation, in five mice on the 7th day, and in two mice on the 8th day.

The hearts transplanted in all individuals in group (b) in which both the donor and recipient mice received ALA (100 mg/kg) stopped beating up to the 8th day. Long-term beating was seen in none of these individuals. More specifically, each heart graft stopped beating in two mice on the 7th day and in three mice on the 8th day.

Long-term beating was found in some individuals in group (c) in which both the donor and recipient mice received ALA (100 mg/kg)+SFC (11.5 mg/kg). More specifically, each heart graft stopped beating in one mouse on the 8th day and in one mouse on the 12th day. The heart graft in one individual still beat when 25 days had passed, and the heart grafts in two individuals still beat when 29 days had passed.

The heart grafts were confirmed to continue long-term beating in a significantly large number of individuals in group (d) in which both the donor and recipient mice received ALA (100 mg/kg)+SFC (115 mg/kg). Many individuals were alive for a long period. More specifically, the heart grafts in two individuals still beat when 63 days had passed and when 73 days had passed. The heart graft in one individual still beat when 93 days had passed and when 103 days had passed.

Long-term beating was confirmed in some individuals in group (e) in which only the recipient mice received ALA (100 mg/kg)+SFC (115 mg/kg). More specifically, the heart graft stopped beating in one mouse on the 15th day, whereas the heart grafts in two individuals still beat when 29 days had passed.

The comparison among groups (b), (c), and (d) demonstrated that in the case where ALAs were administered to donors before transplantation and to recipients after transplantation, the administration of ALA in combination with the iron compound significantly increased an immunosuppressive effect and enhanced the survival rate of the recipients, compared with the administration of ALAs alone. In view of the amount of the iron compound added, group (d) that received 115 mg/kg of sodium ferrous citrate was confirmed to have favorable results. Long-term beating was also found in some mouse individuals in group (e), demonstrating that the agent for promoting graft survival of the present invention was effective even when administered only to recipients after transplantation.

EXAMPLE 3

[Mechanism of Graft Survival is Based on Immune Tolerance]

Figure 4:
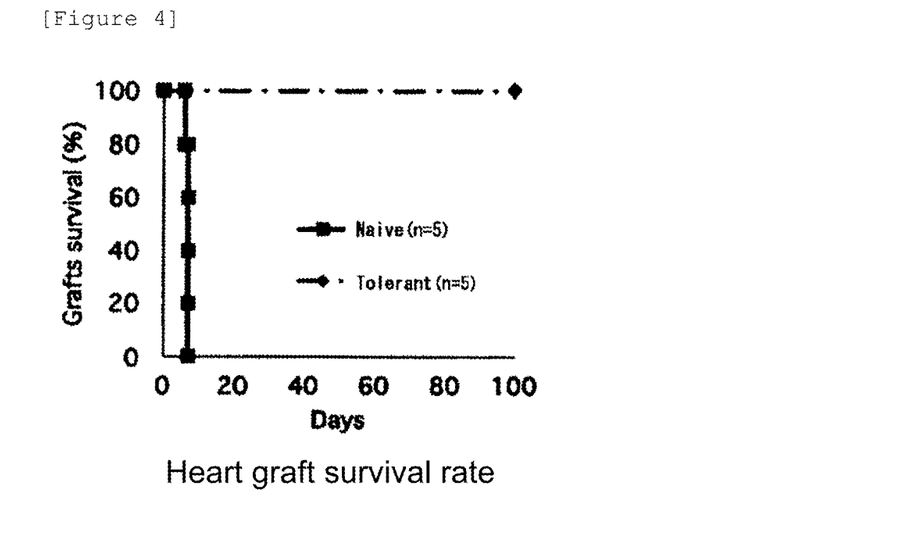
FIG. 4 is a diagram showing results of a heart graft survival rate, wherein the agent for promoting graft survival of the present invention was administered to donor mice and recipient mice before organ transplantation and to the recipient mice after organ transplantation, and spleen cells derived from the recipients were transplanted into recipient mice of the same strain thereas, followed by heart transplantation into these recipient mice from donor mice of different strains therefrom.

ALA (100 mg/kg)+SFC (115 mg/kg) were administered to both donor and recipient mice from 2 days before heart transplantation to the transplantation date and continuously administered after heart transplantation only to the recipient mice once a day until the 11th day. Spleen cells derived from the first transplantation recipient mice (CBA) with long-term graft survival (>100 days) were isolated and intraperitoneally injected into other recipient mice of this strain (CBA) at the same time with the transplantation of the hearts from donor mice (B10) of the same strain as in the first transplantation into the recipient mice of CBA strain. The results are shown in FIG. 4. As a result, the transplantation of the spleen cells that underwent ALA+SFC-administered heart transplantation promoted a graft survival rate after the second heart transplantation (secondary induction of immune tolerance). Specifically, mice (Tolerant; n=5) that simultaneously received the hearts of donor mice (B10) and the spleen cells derived from the first transplantation recipient mice of CBA strain was superior in heart graft survival rate to mice (Naive; n=5) that simultaneously received the hearts of donor mice (B10) and spleen cells derived from recipient mice of CBA strain without the first transplantation. This result indicates that the mechanism of graft survival is based on immune tolerance.

[Mice with Graft Survival Exhibit Immune Tolerance at Individual Level]

Figure 5:
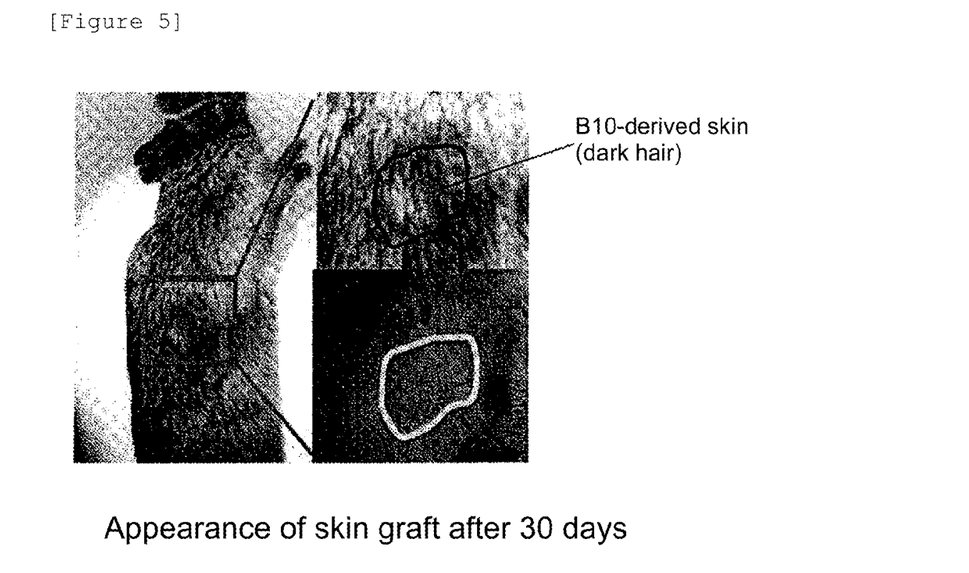
FIG. 5 is a diagram showing a photograph, wherein the agent for promoting graft survival of the present invention was administered to donor mice and recipient mice before organ transplantation and to the recipient mice after organ transplantation, and spleen cells derived from the recipients were transplanted into recipient mice of the same strain thereas, followed by skin transplantation into these recipient mice from donor mice of different strains therefrom.

ALA (100 mg/kg)+SFC (115 mg/kg) were administered to both donor and recipient mice from 2 days before heart transplantation to the transplantation date and continuously administered after heart transplantation only to the recipient mice once a day until the 11th day. Spleen cells derived from the first transplantation recipient mice (CBA) with long-term graft survival (>100 days) were isolated and intraperitoneally injected into other recipient mice of this strain (CBA) at the same time with the transplantation of the skins from donor mice (B10) of the same strain as in the first transplantation into the recipient mice of CBA strain. The results obtained 30 days after the skin transplantation are shown in FIG. 5. As a result, skin graft survival was observed by the transplantation of the spleen cells that underwent ALA+SFC-administered heart transplantation. This result indicates that immune tolerance occurs in mice with graft survival at an individual level.

[The Number of Regulatory T Cells in Spleen]

Figure 6:
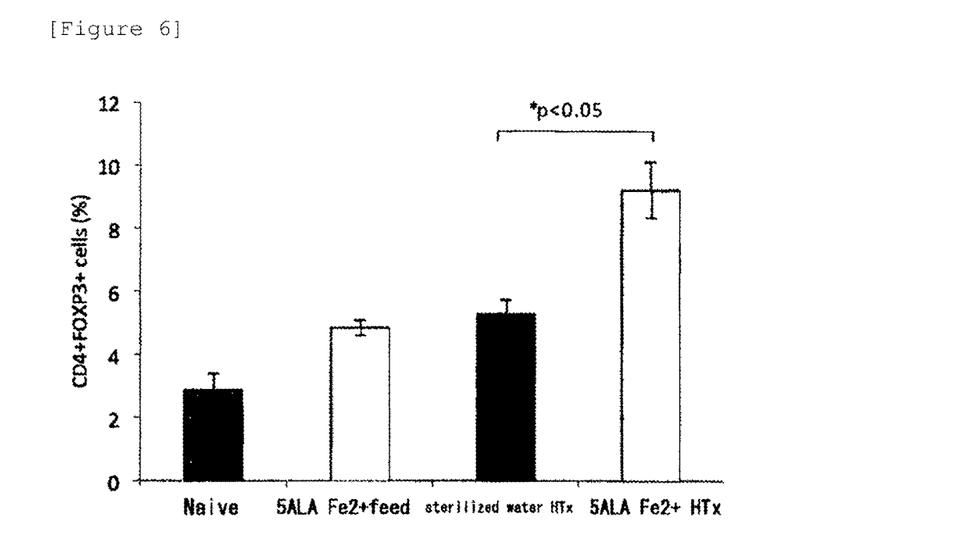
FIG. 6 is a diagram showing results of counting the number of regulatory T cells in recipient-derived spleen cells, wherein the agent for promoting graft survival of the present invention was administered to donor mice and the recipient mice before organ transplantation and to the recipient mice after organ transplantation.

The number of regulatory T cells in the spleens of recipient mice of CBA strain was counted using a flow cytometer. Test recipient mice were prepared as follows: in group 1), only sterilized water was administered to recipient mice (n=6); in group 2), ALA (100 mg/kg)+SFC (115 mg/kg) were administered to recipient mice (n=6); in group 3), sterilized water was administered to both donor and recipient mice, and spleen cells derived from these first heart transplantation recipient mice (CBA) were intraperitoneally injected into other recipient mice of this strain (n=6); and in group 4), ALA (100 mg/kg)+SFC (115 mg/kg) were administered to both donor and recipient mice from 2 days before heart transplantation to the transplantation date and continuously administered after heart transplantation only to the recipient mice once a day until the 11th day, and spleen cells derived from these first heart transplantation recipient mice (CBA) were intraperitoneally injected into other recipient mice of this strain (n=6). The results are shown in FIG. 6. As a result, the number of regulatory T cells in the recipient mice of group 4) was significantly larger than that of group 3), demonstrating that the ratio of the regulatory T cells was increased in the spleen. This result indicates that ALA+SFC administration induces immune tolerance.

EXAMPLE 4

[Effect of ALA-containing Preservation Solution on Preservation and Transplantation of Heart]

The ALA-containing agent for preserving an organ excised from a donor was examined for its efficacy on the maintenance of organ freshness. The maintenance of organ freshness was determined on the basis of the time (second) required for the heart that stopped beating during preservation to start beating again by transplantation, i.e., re-beating time. B10 mice (male, 7 to 10 weeks old, body weight: 20 to 25 g) were used as donors for the hearts to be preserved and transplanted.

The test preservation solutions were prepared as follows: 100 μM ALA and 5 μM iron sulfate (both in terms of final concentration) were added to a basic solution comprising potassium chloride, sodium bicarbonate, dipotassium hydrogen phosphate, potassium dihydrogen phosphate, and glucose to prepare a preservation solution G6(+); and 5 μM iron sulfate (in terms of final concentration) was added to the basic solution to prepare a preservation solution G6(−). The ALA used was ALA hydrochloride. These test preservation solutions had an osmotic pressure of 326 to 363 Osm/kg. A commercially available organ preservation solution ("Viaspan" manufactured by Astellas Pharma Inc.; preservation solution UW) was used as a control. The temperature and preservation period of these preservation solutions were set to ice cooling and 24 hours, respectively.

The re-beating time was determined by testing the preservation solutions G6(+), G6(−), and UW. Also, the determination of the re-beating time followed the description of Experimental Manual of Organ Transplantation (Shujunsha Co., Ltd.), Paragraph 1, Part 2, 2-1-5 "Heterotopic Heart Transplantation in Mice" and European Heart Journal (2011), 32, 509-516. Hereinafter, the procedures will be summarized.

The thorax of each donor mouse was opened under anesthesia and sufficiently perfused using 1 mL of each test preservation solution, followed by excision of the heart. The excised heart was preserved in the test preservation solution. The abdomen of each recipient mouse was opened under anesthesia, and the heart thus excised from the donor mouse and preserved was transplanted into the abdominal vena cava to prepare heterotopic heart-transplanted model mice. The time from the start of blood reperfusion to the heart to the start of heart re-beating was measured and used as re-beating time.

[Shortening of Re-beating Time by ALA-containing Preservation Solution]

Figure 7:
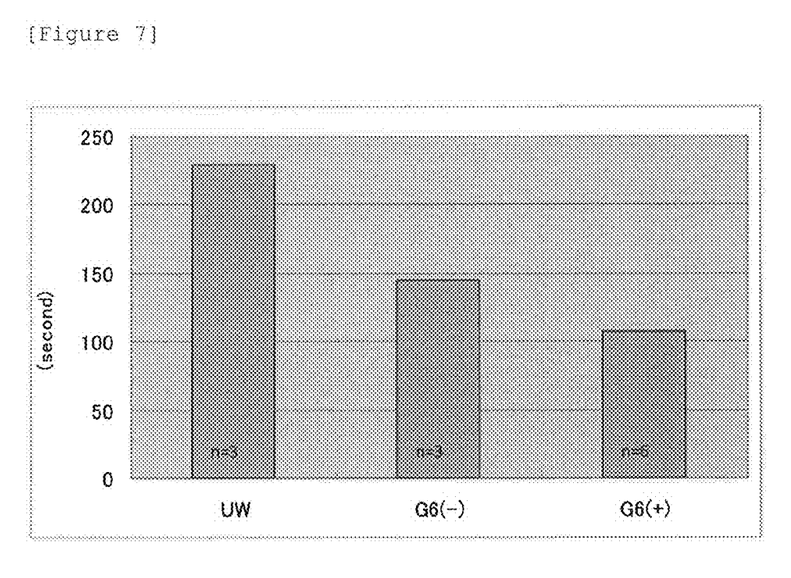
FIG. 7 is a diagram showing results of examining the efficacy of an ALA-containing agent for preserving an organ excised from a donor on the basis of the time (second) required for the heart that stopped beating during preservation to start beating again by transplantation.

Each mouse heart for transplantation was preserved for 24 hours in the preservation solution G6(+), G6(−), or UW, followed by heterotopic homologous heart transplantation and determination of re-beating time (second). The results are shown in FIG. 7. As a result, the average value of re-beating time (second) was 108 seconds for the preservation solution G6(+) consisting of an ALA (100 μM)+iron sulfate (5 μM) solution, 145 seconds for the preservation solution G6(−) consisting of an iron sulfate (5 μM) solution, and 229 seconds for the control preservation solution UW. As is evident from these results, use of the preservation solution G6(+) can significantly (Student's t test; p=0.0244) shorten re-beating time, compared with use of the preservation solution UW.

INDUSTRIAL APPLICABILITY

The agent for promoting graft survival of the present invention can be advantageously used in the pharmaceutical and medical fields.

The invention claimed is:

1. A method for secondary immune tolerance induction, comprising administering an isolated immunocyte derived from a donor to a recipient, wherein an agent for promoting graft survival has been administered to the recipient before and/or after organ transplantation, or the agent has been administered to the donor before organ transplantation and to the recipient before and/or after organ transplantation, the agent comprising a compound represented by the following formula (I) or a salt thereof:

wherein R1 represents a hydrogen atom or an acyl group; and R2 represents a hydrogen atom, a linear or branched alkyl group, a cycloalkyl group, an aryl group, or an aralkyl group.

2. The method for secondary immune tolerance induction according to claim 1, wherein R1 and R2 in the compound represented by formula (I) each represent a hydrogen atom.

3. The method for secondary immune tolerance induction according to claim 1, wherein the agent for promoting graft survival further comprises an iron compound.

4. The method for secondary immune tolerance induction according to claim 3, wherein the iron compound is one or more compound(s) selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

5. The method for secondary immune tolerance induction according to claim 3, wherein the iron compound is sodium ferrous citrate.

6. The method for secondary immune tolerance induction according to claim 2, wherein the agent for promoting graft survival further comprises an iron compound.

7. The method for secondary immune tolerance induction according to claim 6, wherein the iron compound is one or more compound(s) selected from ferric chloride, iron sesquioxide, iron sulfate, ferrous pyrophosphate, ferrous citrate, iron sodium citrate, sodium ferrous citrate, iron ammonium citrate, ferric pyrophosphate, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron sodium dicarboxymethylglutamate, iron ammonium dicarboxymethylglutamate, ferrous fumarate, iron acetate, iron oxalate, ferrous succinate, sodium iron succinate citrate, heme iron, iron dextran, iron triethylenetetramine, lactoferrin iron, transferrin iron, sodium iron chlorophyllin, ferritin iron, saccharated iron oxide, and iron glycine sulfide.

8. The method for secondary immune tolerance induction according to claim 6, wherein the iron compound is sodium ferrous citrate.

9. The method for secondary immune tolerance induction according to claim 1, wherein the isolated immunocyte is a regulatory T cell.

10. The method for secondary immune tolerance induction according to claim 2, wherein the isolated immunocyte is a regulatory T cell.

11. The method for secondary immune tolerance induction according to claim 3, wherein the isolated immunocyte is a regulatory T cell.

12. The method for secondary immune tolerance induction according to claim 4, wherein the isolated immunocyte is a regulatory T cell.

13. The method for secondary immune tolerance induction according to claim 5, wherein the isolated immunocyte is a regulatory T cell.

14. The method for secondary immune tolerance induction according to claim 6, wherein the isolated immunocyte is a regulatory T cell.

15. The method for secondary immune tolerance induction according to claim 7, wherein the isolated immunocyte is a regulatory T cell.

16. The method for secondary immune tolerance induction according to claim 8, wherein the isolated immunocyte is a regulatory T cell.

* * * * *